United States Patent [19]

Lunn et al.

[11] 4,396,619

[45] Aug. 2, 1983

[54] CEPHALOSPORIN BETAINES

[75] Inventors: William H. W. Lunn; John K. Shadle, both of Indianapolis, Ind.

[73] Assignee: Eli Lilly and Company, Indianapolis, Ind.

[21] Appl. No.: 300,100

[22] Filed: Sep. 8, 1981

[51] Int. Cl.³ ............... A61K 31/545; A61K 501/46
[52] U.S. Cl. .................................... 424/246; 544/22
[58] Field of Search ......................... 544/22; 424/246

[56] References Cited

U.S. PATENT DOCUMENTS

| | | | |
|---|---|---|---|
| 4,098,888 | 7/1978 | Ochiai et al. | 424/246 |
| 4,152,432 | 5/1979 | Heymes et al. | 424/246 |
| 4,160,830 | 7/1979 | Morimoto et al. | 424/246 |
| 4,200,575 | 4/1980 | Numata et al. | 424/246 |
| 4,260,747 | 4/1981 | Heymes et al. | 544/27 |
| 4,264,595 | 4/1981 | Numata et al. | 424/246 |
| 4,278,793 | 7/1981 | Durckheimer et al. | 544/28 |

Primary Examiner—Paul M. Coughlan, Jr.
Attorney, Agent, or Firm—William B. Scanlon; Arthur R. Whale

[57] ABSTRACT

Broad spectrum cephalosporin betaine antibiotics represented by the formula

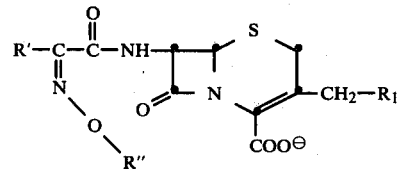

wherein R' is a heterocyclic ring, e.g. 2-aminothiazol-4-yl, 2-amino-1,3,5-thiadiazol-4-yl, or 2-aminopyridin-6-yl; R'' is $C_1$–$C_4$ alkyl, especially methyl, a substituted carbamoyl group, or a carboxy-substituted alkyl or cycloalkyl group; and $R_1$ is isoquinolinium or a substituted isoquinolinium group are provided. Compounds wherein $R_1$ is isoquinolinium are preferred especially syn-7-[2-(2-aminothiazol-4-yl)-2-methoxyiminoacetamido]-3-(isoquinolinium-2-ylmethyl)-3-cephem-4-carboxylate. Pharmaceutical formulations and a method for treating infectious diseases comprising the use of the antibiotics are described.

22 Claims, No Drawings

CEPHALOSPORIN BETAINES

BACKGROUND OF THE INVENTION

This invention relates to semi-synthetic cephalosporin antibiotic compounds. In particular, it relates to cephalosporin compounds wherein the cephalosporin bicyclic nucleus, the 3-cephem nucleus, is substituted in the 3'-position by isoquinolinium and substituted isoquinolinium, and in the 7-position with a 2-heterocyclic-2-oximinoacetamido group.

Cephalosporin compounds substituted in the 3'-position with a quaternary ammonium group have been known for some time. For example, cephalosporin CA (pyridine) was one of the first derivatives of cephalosporin C prepared by Abraham et al. following the discovery of cephalosporin C, Hale, Newton, and Abraham, Biochem. J., 79, 403 (1961).

Cephaloridine, the well-known clinical anti-biotic, is the 3'-pyridinium cephalosporin, 7-($\alpha$-thienylacetamido)-3-(pyridinium-1-ylmethhyl)-3-cephem-4-carboxylate. Recently, Heymes et al., U.S. Pat. No. 4,152,432, describe semi-synthetic cephalosporin antibiotics wherein the 7-position side chain is a 7-[2-(2-(aminothiazol-4-yl)-2-alkoxyiminoacetamido] group. More recently, Takeda, U.K. Patent Specification No. 1,581,854, describes syn-7-[2-(2-aminothiazol-4-yl)-2-methoxyimino]-3-pyridiniummethyl-3-cephem-4-carboxylic acid. O'Callaghan, et al., in U.S. Pat. No. 4,258,041, describe 7-[2-(2-aminothiazole-4-yl)-2-oximinoacetamido]-3-(pyridinium-1-ylmethyl)-3-cephem-4-carboxylate antibiotics, and the corresponding compounds wherein the pyridinium group in the 3'-position is substituted with a carbamoyl group.

Because of the continuing need for improved antibiotic therapy in clinical practice, the search continues for broad spectrum antibiotics with greater potency and minimal toxicity. The semi-synthetic cephalosporin antibiotics long have been recognized as broad spectrum antibiotics, and several have achieved clinical importance. Continued research with the cephalosporin antibiotics has centered of late with the development of antibiotics having higher activity against certain gram-negative microorganisms such as pseudomonas and those which produce $\beta$-lactamase destructive of $\beta$-lactam antibiotics.

SUMMARY OF THE INVENTION

This invention provides broad spectrum cephalosporin antibiotics represented by the following structural formula

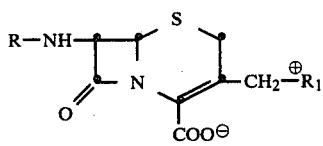

wherein R represents hydrogen or a 2-(5- or 6-membered nitrogen containing heterocyclic ring)-2-oximinoacetyl group, and $R_1$ represents isoquinolinium or substituted isoquinolinium. R in formula 1 can be, for example, the 7-[2-(2-aminothiazol-4-yl)-2-methoxyiminoacetyl], or the 7-[2-(2-aminopyridyl-6-yl)-2-methoxyiminoacetyl] group.

The compounds of formula 1 are prepared by the reaction of the corresponding 3-iodomethylcephalosporin with the desired isoquinoline group.

Preferred compounds of the invention are represented by the above formula wherein $R_1$ is isoquinolinium or amino-substituted isoquinolinium.

The compounds of the invention and pharmaceutical formulations comprising the compounds of the invention are useful in combating infections caused by both gram-positive and gram-negative microorganisms.

DETAILED DESCRIPTION OF THE INVENTION

The cephalosporin antibiotic compounds of this invention are represented by the following structural formula 1

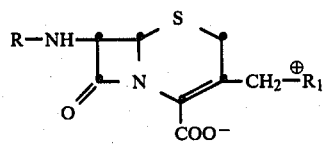

wherein R is hydrogen, formyl or an acyl group of the formula

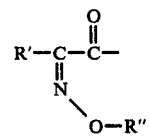

wherein R' is an amino-substituted heterocyclic ring represented by the formulas

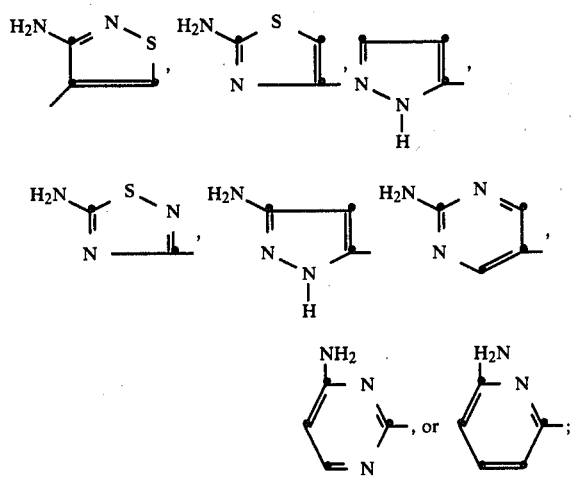

R" is hydrogen, $C_1$–$C_4$ alkyl, a carboxy-substituted alkyl or a carboxy-substituted cycloalkyl group represented by the formula $$-\overset{a}{\underset{b}{C}}-(CH_2)_n-COR'''$$

wherein a and b when taken separately are independently hydrogen or $C_1$–$C_3$ alkyl, and a and b when taken together with the carbon atom to which they are bonded form a $C_3-C_7$ carboxylic ring; n is 0-3; and $R'''$ is hydroxy, $C_1-C_4$ alkoxy, or amino; or $R''$ is a substituted carbamoyl group represented by the formula

wherein $R''''$ is $C_1-C_4$ alkyl, phenyl or $C_1-C_3$ alkyl substituted by phenyl; $R_1$ is isoquinolinium or substituted isoquinolinium, substituted by amino, $C_1-C_4$ alkylamino, di-($C_1-C_4$ alkyl) amino, hydroxy, $C_1-C_4$ alkoxy, halogen, $C_1-C_4$ alkyl, cyano, trifluoromethyl, sulfo ($-SO_3H$), aminosulfonyl ($-SO_2NH_2$), carboxy, $C_1-C_4$ alkoxycarbonyl, hydroxy substituted $C_1-C_3$ alkyl, formyl, $C_2-C_4$ alkanoyl, thiocarbamoyl, or carbamoyl; and the pharmaceutically acceptable non-toxic salts thereof.

The terms employed in the definition of the compounds represented by formula 1 have the following meanings. "$C_1-C_4$ alkyl" refers to the straight and branched chained alkyl hydrocarbon chains such as methyl, ethyl, n-propyl, iso-propyl, n-butyl, t-butyl, and the like; "$C_1-C_4$ alkoxy" refers to methoxy, ethoxy, n-propoxy, isopropoxy, n-butoxy, t-butoxy, and the like; "halogen" refers to fluoro, chloro, or bromo; "$C_1-C_4$ alkylamino" refers to methylamino, ethylamino, n-propylamino, isopropylamino, n-butylamino, isobutylamino, and the like; and "di($C_1-C_4$ alkyl)amino" refers to dimethylamino, diethylamino, di-(n-propyl)amino, di-(n-butyl)amino, and the like; "$C_1-C_4$ alkoxycarbonyl" refers to methoxycarbonyl, ethoxycarbonyl, isopropoxycarbonyl, t-butyloxycarbonyl, and the like; "hydroxy substituted $C_1-C_3$ alkyl" refers to hydroxymethyl, 2-hydroxyethyl, 1-hydroxyethyl, 3-hydroxypropyl, 2-hydroxypropyl, and the like; and "$C_2-C_4$ alkanoyl" refers to acetyl, propionyl, butyryl, iso-butyryl, and the like.

As described above, the compounds of the invention have a quaternary isoquinolinium group in the 3'-position as represented by the term "$\oplus R_1$". As such, the compounds are also referred to as cephalosporin betaines characterized by the $C_4$ carboxylate anion and the quaternary isoquinolinium group in the 3'-position. Illustrative of these 3'-isoquinolinium groups are the amino-substituted isoquinolinium groups such as 4-aminoisoquinolinium, 5-aminoisoquinolinium, 7-aminoisoquinolinium, and like groups; the $C_1-C_4$ alkylamino-substituted isoquinolinium groups such as 4-methylaminoisoquinolinium, 5-ethylaminoisoquinolinium, 6-methylaminoisoquinolinium, 4-(n-butyl)aminoisoquinolinium, 5-isopropylaminoisoquinolinium, 7-methylaminoisoquinolinium, and the like; the di($C_1-C_4$ alkyl)amino-substituted isoquinolinium groups such as 4-diethylaminoisoquinolinium, 4-dimethylaminoisoquinolinium, 5-dimethylaminoisoquinolinium, 6-dimethylaminoisoquinolinium, 4-di-(n-butyl)aminoisoquinolinium, 7-di-(n-propyl)aminoisoquinolinium, and the like; the hydroxy-substituted isoquinolinium groups such as 4-hydroxyisoquinolinium, 5-hydroxyisoquinolinium, 7-hydroxyisoquinolinium, 8-hydroxyisoquinolinium, and the like; isoquinolinium groups substituted by the sulfonic acid group (sulfo) such as isoquinolinium-5-sulfonic acid, isoquinolinium-6-sulfonic acid, isoquinolinium-4-sulfonic acid, and the like; the aminosulfonyl-substituted isoquinolinium groups such as isoquinolinium-5-sulfonamide, isoquinolinium-4-sulfonamide, and the like; the carbamoyl and thiocarbamoyl-substituted isoquinolinium groups such as 5-carbamoylisoquinolinium, 4-carbamoylisoquinolinium, 4-thiocarbamoylisoquinolinium, 6-carbamoylisoquinolinium, and the like; the lower alkyl-substituted isoquinolinium groups such as 8-methylisoquinolinium, 3-methylisoquinolinium, 4-ethylisoquinolinium, 5-methylisoquinolinium, 1,5-dimethylisoquinolinium, and the like; the halo-substituted isoquinolinium groups such as 5-chloroisoquinolinium, 5-bromoisoquinolinium, 5-fluoroisoquinolinium, 6-chloroisoquinolinium, 7-fluoroisoquinolinium, and like halogen-substituted isoquinolinium groups; the carboxy-substituted isoquinolinium groups such as 4-carboxyisoquinolinium, 5-carboxyisoquinolinium, 7-carboxyisoquinolinium, and the like; the $C_1-C_4$ alkoxycarbonyl-substituted isoquinolinium groups, such as 4-methoxycarbonylisoquinolinium, 5-ethoxycarbonylisoquinolinium, 7-t-butyloxycarbonylisoquinoliniu, and the like; the $C_1-C_4$ alkoxy-substituted isoquinolinium groups such as 4-methoxyisoquinolinium, 4-isopropoxyisoquinolinium, 5-ethoxyisoquinolinium, 6-t-butyloxyisoquinolinium, 7-methoxyisoquinolinium, and the like; the cyanoisoquinolinium groups such as 4-cyanoisoquinolinium, 5-cyanoisoquinolinium, 7-cyanoisoquinolinium, and the like; the hydroxyalkyl substituted isoquinolinium groups such as 5-hydroxymethylisoquinolinium, 5-hydroxyethylisoquinolinium, 4-(3-hydroxypropyl)isoquinolinium, 6-(2-hydroxypropyl)isoquinolinium, and the like; the $C_2-C_4$ alkanoyl substituted isoquinolinium groups such as 5-acetylisoquinolinium, 4-propionylisoquinolinium, 7-butyrylisoquinolinium, 6-acetylisoquinolinium, and the like; and the trifluoromethyl-substituted isoquinolinium groups such as 4-trifluoromethylisoquinolinium, 6-trifluoromethylisoquinolinium, 5-trifluoromethylisoquinolinium and like groups.

When in the above formula 1, $R'''$ is hydroxy, the carboxy group of the carboxy-substituted alkyl or carboxy-substituted cycloalkyl group can be protected with a carboxy-protecting group during the synthesis of such compounds of formula 1. Carboxy-protecting groups which are suitable include the well-known carboxy-protecting groups useful for the temporary protection of the $C_4$ carboxy group of the cephalosporin antibiotics. Such groups are, for example, benzyl and substituted benzyl, for example, p-methoxybenzyl, p-nitrobenzyl, diphenylmethyl (benzhydryl), 4-methoxydiphenylmethyl, 4,4'-diphenylmethyl, t-butyl, the halo-substituted alkyl-protecting groups such as 2-iodoethyl, 2,2,2-trichloroethyl, 2,2,2-tribromoethyl, and like carboxy-protecting groups.

The compounds of the invention form acid addition salts owing to the basicity of the amino-substituted heterocyclic in the 7-position side chain. Salts formed with such acids as hydrochloric acid, hydrobromic acid, sulfuric acid, and phosphoric acid can be prepared and are included in this invention. Likewise, salts with the strong organic acids such as the sulfonic acids, for example, methane sulfonic acid, benzene sulfonic acid, and toluenesulfonic acid are suitable acid addition salts.

Examples of the carboxy-substituted alkyl and carboxy-substituted cycloalkyl groups represented by the term "$R''''$" are carboxymethyl, carboxyethyl, carboxypropyl, 2-carboxypropyl, 2-carboxybutyl, 3-carboxypentyl, 1-carboxycyclobutan-1-yl, 1-carboxycyclopentan-1-yl, 1-carboxycyclohexan-1-yl, and the like, as well as the carboxy-protected ester derivatives thereof; and when R''' is $C_1$–$C_4$ alkoxy, examples of such esterified carboxy groups R'' are methoxycarbonylmethyl, ethoxycarbonylmethyl, 1-ethoxycarbonylcyclobut-1-yl, isoproponycarbonylethyl, and the like.

Examples of substituted carbamoyl groups represented by R'' include N-methylcarbamoyl, N-ethylcarbamoyl, N-isopropylcarbamoyl, N-n-butylcarbamoyl, N-phenylcarbamoyl, N-benzylcarbamoyl, N-(2-phenylethyl)-carbamoyl, N-(3-phenylpropyl)carbamoyl, N-(2-phenylpropyl)carbamoyl, and the like.

The 7-acylamino-3'-isoquinolinium compounds of the invention are illustrated by the following structural formula wherein $R_2$ represents the substituent group of the substituted isoquinolinium as defined above.

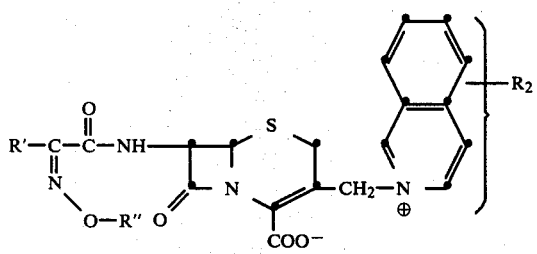

The substituent $R_2$ can be located on either ring of the isoquinolinium bicyclic. In the above formula, R' is the 5- or 6-membered heterocyclic ring as defined above, for example, R' is 2-aminothiazole-4-yl, 2-amino-1,3,5-thiadiazol-4-yl, 2-aminopyrimidin-5-yl, 4-aminopyrimidin-2-yl, 2-aminopyridin-6-yl, 3-aminopyrazol-5-yl, or pyrazol-5-yl.

The compounds of the invention are prepared with the corresponding 7-acylamino-3-acetoxymethylcephalosporin by converting the 3-acetoxymethyl group thereof to a 3-halomethyl derivative, and thereafter reacting the 3-halomethyl derivative with the isoquinoline or substituted isoquinoline to obtain a compound of the invention. The method of preparation is illustrated by the following reaction scheme in which isoquinoline is used.

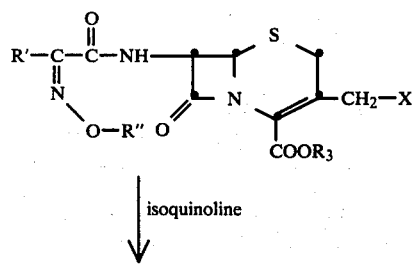

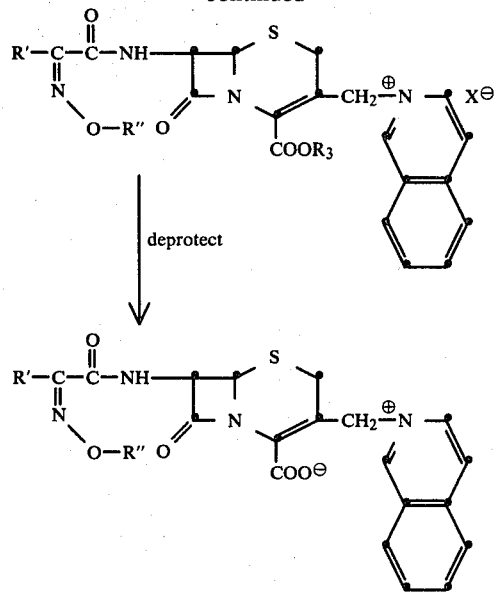

In the above formulas, R' and R'' have the same meanings as defined hereinabove, X is chloro, bromo, or iodo, and $R_3$ is a carboxy-protecting group. The amino group of the amino-substituted heterocyclic R' is also protected during the reaction. The amino group can be protected suitably by trityl or an alkoxycarbonyl protecting group such as t-butyloxycarbonyl, or t-amyloxycarbonyl, or an arylalkoxycarbonyl group such as benzyloxycarbonyl or p-nitrobenzyloxycarbonyl; or preferably by a silyl protecting group such as a trialkylsilyl group, eg. trimethylsilyl.

The carboxy-protecting group $R_3$ is preferably a readily removable ester function conventionally used for the temporary protection of the $C_4$ carboxy group of the cephalosporins. Examples of these ester groups are recited hereinabove for the term R'''. Silyl esters such as the trimethylsilyl ester are preferred.

The preferred method for preparing the compounds of the invention comprises the use of a 7-acylamino-3-iodomethyl derivatives wherein the carboxy and amino groups are protected by silylation such as with a lower trialkylsilyl group, preferably trimethylsilyl. In carrying out the preparation of a compound of the invention by the preferred method, the 7-acylamino-3-acetoxymethyl-4-carboxylic acid is first silylated to block the reactive carboxyl and amino functional groups present in the molecule. The silylation is carried out with one of the commonly employed silylating agents, for example, mono- or bis-trimethylsilylacetamide or, preferably, with mono- or bis-trimethylsilyltrifluoroacetamide. The silylation is carried out in an inert solvent such as a halogenated hydrocarbon solvent, for example, methylene chloride, chloroform, chloroethane, or other inert organic solvent such as acetonitrile or propionitrile. The silylated derivative is then allowed to react with trimethylsilyliodide to form the corresponding 3-iodomethyl silylated derivative. The reaction mixture containing the silylated 3-iodomethyl derivative is evaporated to remove the solvent, and the concentrate is dissolved in acetonitrile and is treated with a slight excess of tetrahydrofuran to degrade any excess TMSI remaining. To this solution is then added isoquinoline, or the substituted derivative thereof to form a compound of formula 1 as the silylated derivative. Upon the addition of water, the silyl derivatives are hydrolyzed to form a compound of the invention.

The following reaction scheme, wherein isoquinoline or a substituted isoquinoline is employed as an example, illustrates the preparation of the compounds of the invention.

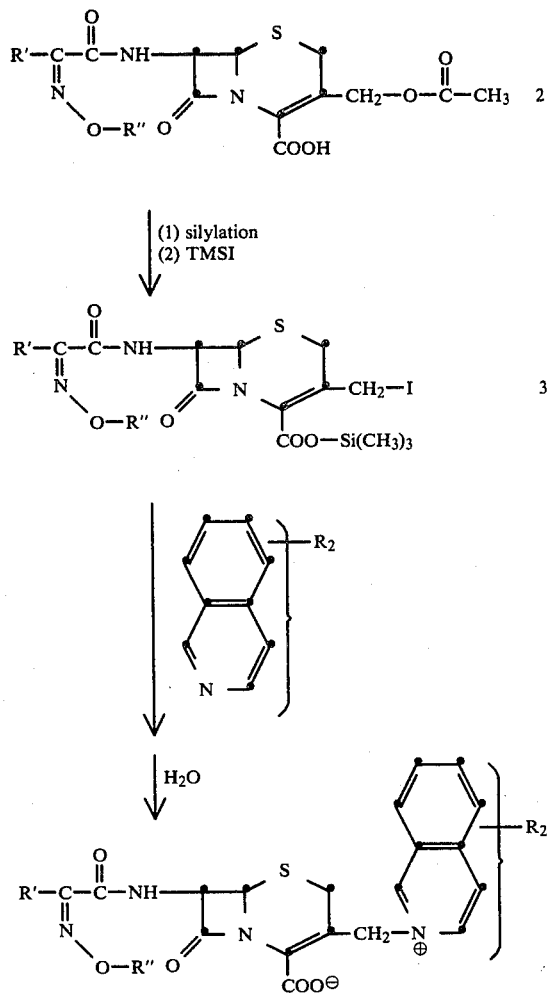

The preparation of the 3-iodomethylcephalosporin intermediate is carried out according to the process described by Bonjouklian in U.S. Pat. No. 4,266,049, issued May 8, 1981. In carrying out the preparation of the 3-iodomethylcephalosporin, other trialkylsilyl iodides may be employed as described by Bonjouklian. Trimethylsilyl iodide is the preferred reagent and is used to illustrate the preparation of the compounds herein.

Compounds represented by the formula 2 which have groups reactive toward the trialkylsilyliodide, are protected by silylation prior to reaction with silyliodide. For example, when in formula 2 R″ is hydrogen, a carboxy-substituted alkyl or carboxy-substituted cycloalkyl group and R‴ is OH, the free oxime hydroxy group and the free carboxylic acid functions are blocked from reaction with the silyl iodide by first silylating the starting material with a silylating agent such as bis-trimethylsilyltrifluoroacetamide (BSTFA) or other suitable silylating reagent. Likewise the amino group of the amino-substituted heterocyclic ring in the 7-position side chain is protected by silylation unless already protected for purposes of the preparation of the compound of formula 2.

In an example of the preparation of a compound of the invention, syn-7-[2-(2-aminothiazol-4-yl)-2-methoxyiminoacetamido]-3-acetoxymethyl-3-cephem-4-carboxylic acid is suspended in an inert organic solvent such as chloroform and is silylated by employing N-methyl-N-trimethylsilyltrifluoroacetamide. A complete solution is obtained upon silylation. To the solution is then added a trialkylsilyl iodide in at least a stoichiometric amount and, preferably, 2 to 3 times the stoichiometric amount. The mixture is stirred to assure complete formation of the 3-iodomethyl derivative. The 3-iodomethyl derivative need not be isolated and, preferably, is used as the silylated derivative in the next step of the reaction. Accordingly, the reaction mixture containing the silylated 3-iodomethyl derivative is evaporated to remove volatiles, for example, solvent, and is then dissolved in acetonitrile. To the solution is added tetrahydrofuran and the solution is stirred for a short while. The treatment of the silylated 3-iodomethyl derivative solution with tetrahydrofuran degrades any remaining trialkylsilyl iodide. The degradation enhances the recovery and purity of the final product.

The solution of the silylated 3-iodomethyl derivative is then mixed with a solution of the isoquinoline or substituted isoquinoline in a suitable solvent such as acetonitrile. The reaction of the isoquinoline or substituted isoquinoline occurs readily and most conveniently at room temperature with stirring. After the reaction is complete, water is added to the mixture to hydrolyze the silyl-blocking groups, for example, the silyl ester formed with the $C_4$ carboxylic acid function. Following the addition of the water to the reaction mixture, the product commonly precipitates and is separated by filtration, centrifugation, or other suitable means. The product is generally crude at this stage of its preparation and can be purified by high performance liquid chromatography by reversed-phase $C_{18}$ silica chromatography using a solvent system of acetonitrile/acetic acid/water containing approximately 2% acetic acid and between about 10% and about 20% of acetonitrile.

The compounds of the invention can be prepared alternatively by acylation of a compound of the formula 1 wherein R is hydrogen, a 7-amino-3-isoquinolinium-1-ylmethyl (or substituted isoquinolinium-1-ylmethyl)-3-cephem-4-carboxylate. The 3′-quaternary ammonium substituted nucleus compounds are prepared by reacting 7-aminocephalosporanic acid or a silylated derivatives thereof with isoquinoline or a substituted isoquinoline. The substituted nucleus is then acylated with an oximino-substituted derivative of the desired heterocyclic acetic acid represented by the formula

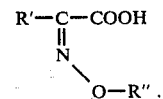

An active derivative of the oximino acetic acid is used in the acylation. For example, the acid group is reacted with hydroxybenzotriazole (HBT) and a carbodiimide such as dicyclohexylcarbodiimide, and the HBT ester used to acylate the 7-amino group of the nucleus. Other active derivatives such as the acid azide, the anhydride formed with methyl chloroformate or isobutyl chloroformate, can be used for acylation.

The compounds of the formula 1 wherein R is hydrogen also can be prepared by the N-deacylation of a 7-acylamino-3-(isoquinolinium or substituted isoquinolinium-1-ylmethyl)-3-cephem-4-carboxylate wherein the 7-acyl group is other than R' (formula 1). The 7-acyl group can be, for example, phenoxyacetyl, phenylacetyl, or 2-thienylacetyl. The N-deacylation is carried out by the well-known procedure for the deacylation of cephalosporins and desacetoxycephalosporins in the preparation of 7-aminocephalosporanic acid and 7-aminodesacetoxycephalosporanic acid. According to the method, a 7-acylaminocephalosporin is reacted with an imino halide-forming reagent, such as phosphorus pentachloride or phosphorus trichloride in the presence of an acid-binding agent, to form the imino chloride of the 7-amido bond. The imino chloride is converted to the imino ether with an alcohol or glycol and the imino ether decomposes to the 7-amino nucleus compound.

In an example of the preparation of a 7-amino-3-(isoquinolinium or substituted isoquinolinium-2-ylmethyl)-3-cephem-4-carboxylate of this invention, 7-(2-thienylacetamido)cephalosporanic acid is reacted with the isoquinoline to form the 7-(2-thienylacetamido)-3-(isoquinolinium-1-ylmethyl)-3-cephem-4-carboxylate. The latter is then converted to the trimethylsilyl ester on reaction in a halogenated hydrocarbon solvent such as methylene chloride or trichloroethane with trimethylchlorosilane in the presence of an amount of dimethylacetamide corresponding to a 4–5 molar excess. The solution of the silyl ester is cooled to a temperature of about $-30°$ C. to about $0°$ C. and an imino halide-forming agent such as phosphorus pentachloride is added. The reaction mixture is stirred in the cold for from 1 to 3 hours.

The cold reaction mixture is then treated with an alcohol such as a $C_1$-$C_4$ alkanol, benzyl alcohol or, preferably, a glycol such as propylene glycol or 1,3-butanediol. The temperature of the reaction mixture is then raised to about $-5°$ C. to about $5°$ C. The product precipitates, is filtered, washed with methylene chloride and dried.

During the N-deacylation any reactive substituent groups of the substituted isoquinolinium group ($R_2$) are protected from reaction with the imino halide-forming reagent. For example, an amino group or carboxy substituent is protected. Since the 7-amino nucleus compound is used in the preparation of compounds of the invention wherein R is an acyl group via the above-described acylation, the protected substituent group is preferably left intact to likewise protect the substituent group during the subsequent N-acylation.

The compounds of the formula 1 wherein R is formyl are useful intermediates for preparing the antibiotic compounds of the invention. They can be used in a method for preparing the 7-amino-nucleus compounds (formula 1, R=H) which is a useful alternative to the side chain N-deacylation method described above.

According to this alternative method, N-formyl 7-aminocephalosporanic acid (7-formamidocephalosporanic acid) is converted to the silylated 3-iodomethyl derivative 7-formamido-3-iodomethyl-3-cephem-4-carboxylic acid silyl ester by the method of Bonjouklian described hereinabove. The 3-iodomethyl derivative is reacted with the isoquinoline or substituted isoquinoline to obtain a compound represented by the formula 1 wherein R is formyl. The N-formyl product is converted to the 7-amino nucleus compound (formula 1, R=H) by hydrolysis in methanolic hydrochloric acid.

The compounds of the invention wherein R is an acyl group can be prepared by another alternative procedure comprising the displacement of the acetoxy group of the desired 7-acylamino-3-acetoxymethyl cephalosporin with isoquinoline or substituted isoquinoline. The reaction is illustrated as follows.

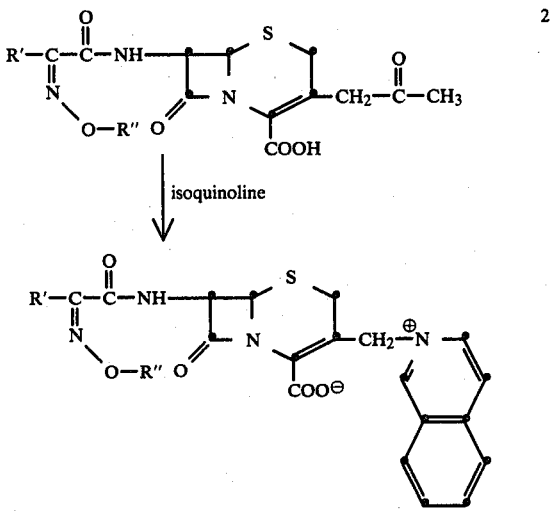

The reaction is carried out in an aqueous solvent system of water and a water miscible organic solvent such as acetone, DMF, DMAC or other suitable solvent at a temperature between about $20°$ C. and about $55°$ C. A small amount of an alkali metal iodide such as sodium iodide is added to the reaction mixture to enhance the reaction rate and yield of the reaction.

The 7-[2-(heterocyclic)-2-oximino- and 2-substituted oximinoacetamido]-3-acetoxymethyl-3-cephem-4-carboxylic acids, represented by the above formula 2, which are used to prepare the compounds of the invention are known or can be prepared as described herein. Heymes, et al., U.S. Pat. No. 4,152,432 describes the compound of formula 2 wherein R' is 2-aminothiazol-4-yl and R'' is lower alkyl; the compounds of the formula 2 wherein R' is 2-aminopyridin-6-yl, 2-aminopyrimidin-5-yl, or 4-aminopyrimidin-2-yl, are described by UK Patent Application No. 2,010,840A, and U.S. Pat. No. 4,267,176; the compound of the formula 2 wherein R' is 5-amino-1,2,4-thiadiazol-3-yl is described by European Patent Application No. 0,007,470; the compound of formula 2 wherein R' is 3-aminopyrazol-5-yl is prepared as described by UK Patent Application No. 2,046,734A.

The compounds of the formula 2 are prepared by acylating 7-aminocephalosporanic acid as illustrated by the following reaction scheme.

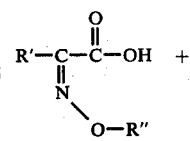

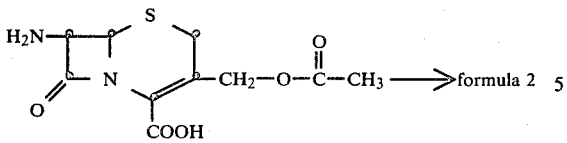 →formula 2

The acylation is preferably carried out with an active derivative of the oximino-substituted acid, for example with an acid halide, acid azide, or an ester. Active esters formed with ethyl chloroformate or isobutyl chloroformate, or with hydroxybenzotriazole (HBT) are suitable in the acylation. The acylation can be carried out in an aqueous or a non-aqueous medium. For non-aqueous acylation a silylated derivative of 7-ACA such as the trimethylsilyl ester derivative which is substantially soluble in organic solvents is employed. When an acid halide is used as the active carboxylic acid derivative, a hydrogen halide acceptor is also used. Acid acceptors such as the tertiary amines such as triethylamine and pyridine are suitable for use in the acylation. Following the acylation, the silyl ester group is hydrolyzed to the free acid form of the compound of formula 1.

Acylation under aqueous conditions can be carried out using the active ester formed with HBT or alternatively with the acid halide in the presence of an acid binding agent such as a tertiary amine or an alkali metal carbamate or bicarbonate e.g. sodium carbonate.

The aqueous acylation with an acid halide can be carried out in an aqueous solvent system comprising a water miscible solvent such as acetone. Solvent suitable for the non-aqueous acylation include tetrahydrofuran, acetonitrile, methylene chloride or other suitable solvent.

Also for purposes of the acylation, the amino group of the heterocyclic ring in the 7-position side chain is protected. A conventional amino-protecting group can be used, for example, trityl; an alkoxycarbonyl or arylalkoxycarbonyl group such as t-butyloxycarbonyl, t-amyloxycarbonyl, benzyloxycarbonyl, p-nitrobenzyloxycarbonyl, 2,2,2-trichloroethoxycarbonyl, and like groups; an acyl group such as chloroacetyl, dichloroacetyl, and the like. Preferably, the amino group is protected by silylation, for example with a trialkylsilyl group such as trimethylsilyl.

The compounds of the formula 1 wherein R' is a pyrazol-5-yl or 3-aminopyrazol-5-yl group are prepared by employing methods known in the art. The 2-(pyrazol-5-yl)-2-oximinoacetic acid or the 2-(3-aminopyrazol-5-yl)-2-oximinoacetic acid is prepared and converted to an active derivative of the carboxylic acid, for example, an active ester. The active ester is coupled, via N-acylation, with 7-aminocephalosporanic acid and the 7-[2-(pyrazol-5-yl)-2-oximinoacetamido]-3-acetoxymethyl-3-cephem-4-carboxylic acid and 7-[2-(3-aminopyrazol-5-yl)-2-oximinoacetamido]-3-acetoxymethyl-3-cephem-4-carboxylic acid are converted to the corresponding 3-iodomethyl silylated derivatves as described herein. The latter are reacted with isoquinoline or the substituted isoquinoline to provide a compound of the invention.

The pyrazole and aminopyrazole oximino substituted acetic acids are prepared by employing synthetic methods known in the art. For example, the 2-(pyrazol-5-yl)-2-alkoxyiminoacetic acid is prepared by heating in an inert hydrocarbon solvent the acetyl oximino compound of the formula A

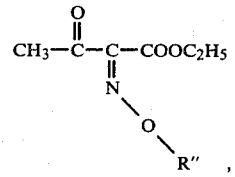

wherein R" is other than hydrogen as defined above, with dimethylformamide dimethylacetal to form the dimethylaminomethylene oximino ester of the formula

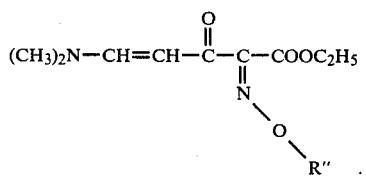

The latter is reacted with hydrazine hydrate to provide the ethyl ester of 2-(pyrazol-5-yl)-2-alkoxyiminoacetic acid. The ester is hydrolyzed to the free acid and the acid converted to an active ester for acylation.

The 2-(3-aminopyrazol-5-yl)-2-alkoxyiminoacetic acid is prepared by reacting the compound of the formula A with carbon disulfide and two equivalents of methyl iodide to form the intermediate compound of the formula B

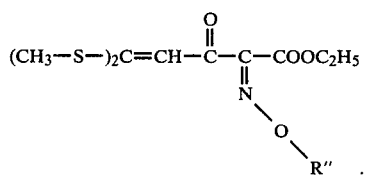

Intermediate B is reacted with N-t-BOC hydrazine to provide compound C,

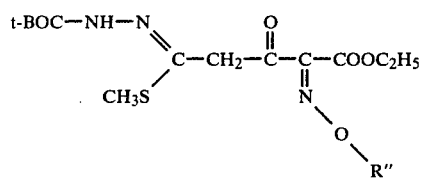

and C is reacted with hydrazine hydrate to form (2-(3-t-BOC-hydrazinopyrazol-5-yl)-2-oximinoacetic acid ethyl ester D.

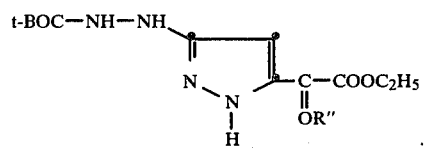

Compound D is treated in the cold with trifluoroacetic acid to remove the t-BOC group and the 3-hydrazinopyrazole is nitrosated with nitrous ($HNO_2$) acid in the cold to form 2-(3-azidopyrazol-5-yl)-2-oximinoacetic acid ethyl ester. The azido group is reduced to the amino group by chemical reduction to provide the 2-(3-aminopyrazol-5-yl)oximinoacetic acid ethyl ester. The ester is then hydrolyzed under alkaline conditions to the free acid.

The compounds of the invention, by virtue of the amino-substituted 5- or 6-membered heterocyclic ring in the 7-position side chain, form acid addition salts as described above. Also, the compounds of the invention wherein R'' is a carboxy-substituted alkyl or carboxy-substituted cycloalkyl group form salts of the carboxylic acid group. Such salts as the alkali metal salts, for example, the sodium salt, potassium salt, and the like, are useful pharmaceutically acceptable salts of this invention which can be used in formulating the compounds for use.

A preferred group of compounds of this invention are represented by formula 1 wherein the oximino group has the syn configuration. A further preferred group of compounds of the invention are those represented by formula 1 wherein $R_1$ is the unsubstituted isoquinolinium group, and the oximino group in the 7-position side chain thereof is in the syn configuration. The isoquinolinium substituted compounds are preferred because of the high activity they possess against gram-negative bacteria in particular pseudomonas and proteus species. These compounds also possess a high order of activity against the gram positive bacteria such as the staphylococci and streptococci. Further, these compounds are preferred because the isoquinoline which would be formed by metabolism of the antibiotics is an especially innocuous aromatic base known to be free of the toxic liability, for example, mutagenicity, inherent in other aromatic bases such as quinoline. These properties of these preferred compounds makes them attractive antibiotics for the treatment of infectious diseases.

Examples of these preferred compounds include the following:

syn-7-[2-(2-aminothiazol-4-yl)-2-methoxyiminoacetamido]-3-(isoquinolinium-2-ylmethyl)-3-cephem-4-carboxylate, syn-7-[2-(2-aminothiazol-4-yl)-2-hydroxyiminoacetamido]-3-(isoquinolinium-2-ylmethyl)-3-cephem-4-carboxylate, syn-7-[2-(2-aminothiazol-4-yl)-2-(2-carboxyprop-2-yl)oxyiminoacetamido]-3-(isoquinolinium-2-ylmethyl)-3-cephem-4-carboxylate, syn-7-[2-(2-aminopyrimidin-5-yl)-2-methoxyiminoacetamido]-3-(isoquinolinium-2-ylmethyl)-3-cephem-4-carboxylate, syn-7-[2-(2-aminopyridin-6-yl)-2-(2-carboxyprop-2-yl)oxyiminoacetamido-]-3-(isoquinolinium-2-ylmethyl)-3-cephem-4-carboxylate, syn-7-[2-(5-amino-1,2,4-thiadiazol-3-yl)-2-methoxyiminoacetamido]-3-(isoquinolinium-2-ylmethyl)-3-cephem-4-carboxylate, syn-7-[2-(5-amino-1,2,4-thiadiazol-3-yl)-2-isopropoxyiminoacetamido]-3-(isoquinolinium-2-ylmethyl)-3-cephem-4-carboxylate, syn-7-[2-(2-aminopyridin-6-yl)-2-methoxyiminoacetamido]-3-(isoquinolinium-2-ylmethyl)-3-cephem-4-carboxylate, syn-7-[2-(4-aminopyrimidin-2-yl)-2-methoxyiminoacetamido]-3-(isoquinolinium-2-ylmethyl)-3-cephem-4-carboxylate, and syn-7-[2-(5-amino-1,2,4-thiadiazol-3-yl)-2-(2-carboxyprop-2-yl)oxyiminoacetamido]-3-(isoquinolinium-2-ylmethyl)-3-cephem-4-carboxylate.

A further preferred group of compounds is represented by formula 1 wherein $R_1$ is an amino-substituted isoquinolinium group. This group of compounds is illustrated in the following Table 1.

TABLE 1

Aminoisoquinolinium Substituted Betaine Cephalosporins

| R' | R'' | Amino position |
|---|---|---|
| 2-aminothiazol-4-yl | CH$_3$ | 5-amino |
| " | " | 4-amino |
| 5-amino-1,2,4-thiadiazol-4-yl | " | 5-amino |
| 5-amino-1,2,4-thiadiazol-4-yl | " | 4-amino |
| 5-amino-1,2,4-thiadiazol-4-yl | " | 6-amino |
| 2-aminopyridin-6-yl | " | 5-amino |
| " | C$_2$H$_5$ | 4-amino |
| " | 2-carboxyprop-2-yl | 6-amino |
| 4-aminopyrimidin-2-yl | " | 4-amino |
| " | CH$_3$ | " |
| 4-aminopyrimidin-2-yl | CH$_3$ | 5-amino |
| " | C$_2$H$_5$ | 4-amino |
| " | 2-carboxyprop-2-yl | 6-amino |
| 3-aminoisothiazol-4-yl | CH$_3$ | 4-amino |
| 3-aminopyrazol-4-yl | CH$_3$ | 4-amino |
| " | " | 5-amino |

A further preferred group of compounds are represented by the formula when R'' is $C_1-C_4$ alkyl. An especially preferred compound is syn-7-[2-(2-aminothiazol-4-yl)-3-methoxyiminoacetamido]-3-(isoquinolinium-2-ylmethyl)-3-cephem-4-carboxylate.

Another preferred group of compounds are represented by the formula 1 wherein $R_1$ is an hydroxy-substituted isoquinolinium group. Examples of preferred compounds of the group are syn-7-[2-(2-aminothiazol-4-yl)-2-methoxyiminoacetamido]-3-(5-hydroxyisoquinolinium-2-ylmethyl)-3-cephem-4-carboxylate and syn-7-[2-(2-aminothiazol-4-yl)-2-methoxyiminoacetamido]-3-(4-hydroxyisoquinolinium-2-ylmethyl)-3-cephem-4-carboxylate.

Among the preferred groups of compounds described above are those wherein the amino-substituted heterocyclic R' is 2-aminothiazol-4-yl, 5-amino-1,2,4-thiadiazol-3-yl, 2-aminopyrimidin-4-yl, and 2-aminopyridin-6-yl.

The compounds represented by the formula 1 wherein R is hydrogen or formyl are useful intermediates for preparing the compounds of formula 1 wherein R is an acyl group as defined hereinabove.

The compounds of the formula 1 wherein R is an acyl group and the pharmaceutically acceptable non-toxic salts thereof are broad spectrum antibiotics which are particularly effective in inhibiting the growth of gram-negative microorganisms pathogenic to man and animals. For example, the compounds are effective against various pseudomonas, hemophilus, proteus, enterobacter, shigella, salmonella, and other gram-negative microorganisms. The 7-acylamino cephalosporin antibiotics of the formula 1 are also effective against streptococcus and staphylococcus organisms including the penicillin-resistant staphylococci.

The antibiotics of formula 1 and the salts thereof are relatively non-toxic. For example, they either lack or display a low order of nephrotoxicity in in vitro tests.

The antibiotic compounds and the pharmaceutically acceptable non-toxic salts thereof represented by the formula 1 wherein R is an acyl group and R''' is other than a carboxy-protecting group can be formulated into antibiotic formulations suitable for administration in the treatment of infectious diseases. In one aspect of this invention there is provided an antibiotic formulation comprising the compound of formula 1 or a pharmaceutically acceptable non-toxic salt thereof wherein R is an acyl group and a pharmaceutical carrier. The antibiotic or preferably a pharmaceutically acceptable salt thereof can be formulated into formulations suitable for parenteral administration i.e. via the i.v., i.m. or s.c. routes. For intravenous use the antibiotic can be formulated with one of the commonly emloyed intravenous fluids and administered by infusion. Such fluids as for example, physiological saline, Ringer's solution or 5% dextrose can be used.

For intramuscular use, the antibiotic can be made up in dosage unit formulations comprising the antibiotic in solid form in sterile vials or ampoules containing from about 100 mg. to about 2 g. per vial or ampoule. Such unit dosages upon dissolution in a suitable diluent such as Water-for-Injection, 5% dextrose, 5% glucose, or other diluent, are administered to the patient with a syringe.

Alternatively the unit dosage form of the antibiotic can be a solution of the antibiotic or preferably a salt thereof in a suitable diluent in sterile, hermetically sealed ampoules. The concentration of the antibiotic in the unit dosage may vary, e.g. from about 2 percent to about 20 percent depending on the particular antibiotics, the solubility thereof and the dose desired by the physician.

The antibiotic compounds of the invention may also be formulated into antiseptic solutions for topical use such as for the treatment and prevention of skin infections. Antibacterial solutions containing the antibiotic or an acceptable non-toxic salt thereof containing the antibiotic at a concentration between about one percent and about twenty five percent may be prepared in an aqueous or non-aqueous diluent. Such diluents as water, ethyl alcohol, mixtures of the former, propylene glycol and like diluents can be used. Solubilizing agents, surfactants, preservatives, stabilizing agents, and coloring agents may be added to such solutions as is well known in the art.

In a further aspect of this invention there is provided a method for the treatment of infectious diseases in mammals which comprises administering to said mammal at a dose between about 100 mg. and about 2000 mg. a compound represented by the formula 1 wherein R is an acyl group and R''' is other than a carboxy-protecting group, or a pharmaceutically acceptable non-toxic salt thereof.

In practicing the above method the antibiotic can be administered in a single daily dose or in multiple doses per day. The treatment regime may require administration over extended periods of time e.g. for several days or for two to three weeks. The amount per administered dose or the total amount administered will depend on such factors as the nature and severity of the infection, the age and general health of the patient, and the tolerance of the patient to the antibiotic.

A convenient method of practicing the treatment method is to administer the antibiotic via i.v. infusion. In this procedure the antibiotic is incorporated in a solution of a physiological fluid, such as 5% dextrose, and the solution infused slowly i.v. Alternatively, the piggy-back method of i.v. infusion can also be employed.

A preferred antibiotic method of this invention comprises administering the antibiotic of the formula 1 wherein the oxime function is in the syn form, R' is the 2-aminothiazol-4-yl group, R'' is $C_1$-$C_4$ alkyl, and $R_1$ is isoquinolinium, an amino-substituted isoquinolinium group or a hydroxy-substituted isoquinolinium group. An especially preferred method comprises administering syn-7-[2-(2-aminothiazol-4-yl)-2-methoxyiminoacetamido]-3-(isoquinolinium-2-ylmethyl)-3-cephem-4-carboxylate.

The following examples further illustrate this invention. In the examples the abbreviations used have the following meanings:

TMSI = trimethylsilyliodide;
HPLC = high performance liquid chromatography;
NMR = nuclear magnetic resonance;
$DMSOd_6$ = deuterated dimethylsulfoxide; and the letters used to characterize the signals in the NMR spectra are as follows: s = singlet; d = doublet; m = multiplet; q = quartet; and bs = broad singlet.

EXAMPLE 1 syn-7-[2-(2-Aminothiazol-4-yl)-2-methoxyiminoacetamido]-3-(isoquinolinium-2-ylmethyl)-3-cephem-4-carboxylate.

To a suspension of 4.09 g (9 mmole) of syn-7-[2-(2-aminothiazol-4-yl)-2-methoxyiminoacetamido]-3-acetoxymethyl-3-cephem-4-carboxylic acid in 18 ml of chloroform were added 5.6 ml of N-methyl-N-trimethylsilyltrifluoroacetamide, and after the mixture was stirred for 1.5 hours a complete solution was obtained. To the solution were added 3.45 ml of trimethylsilyliodide, and after the reaction mixture was stirred for 15 minutes the mixture was evaporated to dryness. The crude silylated 3-iodomethyl derivative was dissolved in 18 ml of acetonitrile and 735 microliters of tetrahydrofuran were added to the solution. The solution was stirred for 5 minutes to destroy any complex of TMSI with the 3-iodomethyl derivative.

One sixth of the solution of the 3-iodomethyl derivative was added to a solution of 232 mg of isoquinoline in 1 ml of acetonitrile, and the mixture was stirred at room temperature for 3 hours. After 145 microliters of water were added to the reaction mixture, the product was filtered and dried. There were obtained 730 mg of the title compound.

NMR ($DMSOd_6$): signals at 9.52 (d, 1H), 9.46 (d, 1H), 8.68-8.08 (m, 6H), 7.17 (bs, 2H), 6.71 (s, 1H), 5.86 (d, 1H), 5.65 (q, 1H), 5.20 (d, 1H), 5.07 (d, 1H), 3.76 (s, 3H), and 3.34 (q, 2H).

EXAMPLE 2 syn-7-[2-(2-Aminothiazol-4-yl)-2-methoxyiminoacetamido]-3-(5-sulfo-isoquinolinium-2-ylmethyl)-3-cephem-4-carboxylate.

To a suspension of 1.82 g of syn-7-[2-(2-aminothiazol-4-yl)-2-methoxyiminoacetamido]-3-acetoxymethyl-3-cephem-4-carboxylic acid in 8 ml of chloroform were added 2.50 ml of N-methyl-N-trimethylsilyltrifluoroacetamide. The mixture was stirred for 1 hour, and to the resultant solution were added 1.54 ml of trimethylsilyliodide. The mixture was stirred at room temperature for 15 minutes, was evaporated to dryness, and the residue of the silylated 3-iodomethyl derivative was dissolved in 8 ml of acetonitrile. To the solution were added 326 microliters of tetrahydrofuran and the solution was stirred for 5 minutes.

One-half of the solution was added to a suspension of 502 mg of isoquinoline-5-sulfonic acid in 2 ml of acetonitrile containing 427 microliters of bis-trimethylsilyltrifluoroacetamide. The reaction mixture was stirred at room temperature for 3 hours and was then treated with 210 μl of water. The title compound was filtered and dried. There were obtained 1.39 g of the crude product which was purified by HPLC to provide 945 mg of the title compound.

NMR (DMOSd$_6$/D$_2$O): signals at 9.75 (s, 1H), 9.04 (d, 1H), 8.75 (d, 1H), 8.58 (m, 2H), 7.97 (m, 1H), 6.70 (s, 1H), 5.73 (d, 1H), 5.55 (d, 2H), 5.12 (d, 1H), 3.73 (s, 3H), and 3.41 (q, 2H).

EXAMPLE 3 syn-7-[2-(2-Aminothiazol-4-yl)-2-methoxyiminoacetamido]-3-(5-aminoisoquinolinium-2-ylmethyl)-3-cephem-4-carboxylate.

A suspension of 11.8 g of syn-7-[2-(2-aminothiazol-4-yl)-2-methoxyiminoacetamido]-3-acetoxymethyl-3-cephem-4-carboxylic acid in 50 ml of chloroform was treated with stirring for 1 hour with 16.25 ml of N-methyl-N-trimethylsilyltrifluoroacetamide. After solution was obtained 10 ml of TMSI were added and the mixture was stirred for 15 minutes and then evaporated to remove volatiles. The residue of the silylated 3-iodomethyl derivative was dissolved in 50 ml of acetonitrile and 2.12 ml of tetrahydrofuran were added to the solution.

One-thirteenth of the silylated 3-iodomethyl solution prepared as described above was added to a solution of 346 mg of 5-aminoisoquinoline in 2 ml of acetonitrile containing 853 μl of bis-trimethylsilyltrifluoroacetamide, and the mixture was stirred for 3 hours at room temperature. After 235 μl of water were added to the mixture by pipette, the title compound was recovered from the mixture by filtration and dried. There were obtained 1.27 g of the impure product which on HPLC yielded 100 mg of purified product.

NMR (DMSOd$_6$/D$_2$O): signals at 9.90 (bs, 1H), 8.96 (d, 1H), 8.55 (d, 1H), 8.00–7.04 (m, 4H), 6.71 (s, 1H), 5.69–5.65 (d, d, 2H), 5.17–5.05 (d, d, 2H), 3.76 (s, 3H), and 3.30 (q, 2H).

EXAMPLE 4 syn-7-[2-(2-Aminothiazol-4-yl)-2-methoxyiminoacetamido]-3-(4-aminoisoquinolinium-2-ylmethyl)-3-cephem-4-carboxylate.

One-thirteenth of the solution of the silylated 3-iodomethyl derivative prepared as described by Example 3 was added to a solution of 346 mg of 4-aminoisoquinoline in 2 ml of acetonitrile containing 853 μl of bis-trimethylsilyltrifluoroacetamide, and the mixture was stirred for 3 hours at room temperature. After 235 μl of water were added by pipette, the title compound was filtered and dried. There were obtained 1.41 g of product which was purified by HPLC.

NMR (DMOSd$_6$): signals at 9.52 (d, 1H), 9.25 (s, 1H), 8.60–7.80 (m, 5H), 7.34 (bs, 2H), 7.17 (bs, 2H), 6.71 (s, 1H), 5.77 (d, 1H), 5.63 (q, 1H), 5.12 (d, 1H), 5.05 (d, 1H), 3.76 (s, 3H), and 3.26 (q, 2H).

EXAMPLE 5 syn-7-[2-(2-aminothiazol-4-yl)-2-methoxyiminoacetamido]-3-(3-methylisoquinolinium-2-ylmethyl)-3-cephem-4-carboxylate.

To a suspension of 4.39 g (9 mmole) of syn-7-[2-(2-aminothiazole-4-yl)-2-methoxyiminoacetamido]-3-acetoxymethyl-3-cephem-4-carboxylic acid in 18.0 ml of chloroform were added 6.45 g (5.76 ml, 32.4 mmole) of N-methyl-N-trimethylsilyltrifluoroacetamide, and the mixture was stirred until complete solution was obtained (1.5 hours). The solution of the silylated derivative was treated with 4.86 g (3.46 ml, 24.3 mmole) of trimethylsilyliodide and the mixture was stirred for 30 minutes. The reaction mixture was evaporated to dryness, and the residue of the silylated 3-iodomethyl derivative was dissolved in 12 ml of dry acetonitrile and 0.972 g (1.09 ml) of tetrahydrofuran. The solution was stirred for 30 minutes prior to use in the reaction next described.

A 4 ml aliquot of the solution of the silylated 3-iodomethyl derivative was mixed with a solution of 3-methylisoquinoline in 1 ml of dry acetonitrile, and the mixture was stirred at room temperature for 3 hours. An additional 1 ml of acetonitrile was added and the mixture chilled. Water (180 μl) was added to the reaction mixture and the precipitate of crude product was separated by filtration. There were obtained 842 mg of precipitate which was chromatographed by HPLC. There were obtained 63 mg of the purified title compound.

NMR (DMSOd$_6$): signals at 9.58 (d, 1H), 8.57–7.90 (m, 6H), 7.20 (bs, 2H), 6.74 (s, 1H), 5.84–5.17 (m, 3H), 5.07 (s, 1H), 3.78 (s, 3H), 3.78 (s, 3H), and 3.30 (q, 2H).

EXAMPLE 6 syn-7-[2-(2-Aminothiazol-4-yl)-2-methoxyiminoacetamido]-3-(8-hydroxyisoquinolinium-2-ylmethyl)-3-cephem-4-carboxylate.

To a suspension of 910 mg (2 mmole) of syn-7-[2-(2-aminothiazol-4-yl)-2-methoxyiminoacetamido]-3-acetoxymethyl-3-cephem-4-carboxylic acid in 5 ml of methylene chloride were added 1.24 ml (7 mmole) of N-methyl-N-trimethylsilyltrifluoroacetamide and the mixture was warmed to 40° C. After a complete solution was obtained it was cooled to room temperature and 0.77 ml (5.4 mmole) of trimethylsilyliodide was added and the reaction mixture stirred under nitrogen at room temperature for 1.5 hours. The reaction mixture was evaporated and the silylated 3-iodomethyl derivative obtained as an oil was dissolved in 10 ml of acetonitrile. The solution was treated with 0.16 ml of tetrahydrofuran to destroy an TMSi complex or excess TMSi present in the solution.

To the above solution of the silylated 3-iodomethyl derivative was added under nitrogen a solution of the trimethylsilyl derivative of 8-hydroxyisoquinoline in acetonitrile (prepared by treating a suspension of 348 mg (2.4 mmole) of 8-hydroxyisoquinoline in 10 ml of acetonitrile with 0.43 ml of mono-trimethylsilyltrifluoroacetamide). The mixture was stirred at room temperature for 2.5 hours and was then diluted with a small amount of diethyl ether and then with water. The product precipitated as a thick, tan precipitate. After stirring the mixture for 10 minutes, the product was separated by filtration and was washed with diethyl ether. The product was dried under vacuum at 40° C. for 1.5 hours to yield 1.27 g of impure product.

The nmr spectrum of the product was in aggreement with its structure.

The product was purified over $C_{18}$ silica reverse phase high performance liquid chromatography using 5% acetonitrile, 2% acetic acid, 93% water. Fractions off the column which by nmr were shown to contain the product were combined and lyophilized. The purified product was obtained as a yellow powder, 470 mg (39% yield).

NMR (DMSOd$_6$): signals at 10.09 (s, 1H), 9.5 (d, 1H), 9.1 (d, 1H), 8.5 (d, 1H), 7.8 (d, 2H), 7.55 (t, 1H), 7.15 (s, 2H), 6.7 (s, 1H), 5.65 (q, 1H), 5.5 (q, 2H), 5.1 (d, 1H), 3.75 (s, 3H), and 3.3 (q, 2H) δ.

UV: $\lambda_{max}$ 254 nm ($\epsilon$=25,000); pKa 3.7, 7.1, 8.5.

EXAMPLE 7 syn-7-[2-(2-Aminothiazol-4-yl)-2-methoxyiminoacetamido]-3-(5-hydroxyisoquinolinium-2-ylmethyl)-3-cephem-4-carboxylate By following the reaction procedures and conditions and by using the same amounts of the starting material and reagents described by Example 6, 5-hydroxyisoquinoline was substituted for the 8-hydroxyisoquinoline of Example 6 to yield 1.31 g. of the crude product. The product was purified by HPLC over $C_{18}$ silica reverse phase, using 10% acetonitrile, 2% acetic acid, 88% water, to provide 636 mg. of the purified product.

NMR (DMSOd$_6$): signals at 10.09 (s, 1H), 9.55 (d, 1H), 9.15 (d, 1H), 8.55 (d, 1H), 7.85 (d, 2H), 7.6 (t, 1H), 7.2 (s, 2H), 6.7 (s, 1H), 5.65 (q, 1H), 5.5 (q, 2H), 5.1 (d, 1H), 3.75 (s, 3H), and 3.35 (q, 2H) δ.

UV: $\lambda_{max}$ 254 nm ($\epsilon$=23,893); pKa 3.7, 7.0, 8.5.

Further examples of compounds of the formula 1 which can be prepared by following the procedures and reaction conditions described by the preceding examples are listed below.

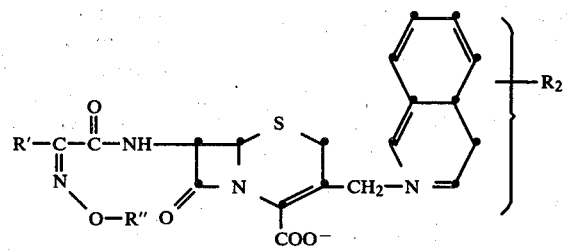

| Example No. | R' | R'' | R$_2$ |
|---|---|---|---|
| 8 | 2-aminothiazol-4-yl | CH$_3$ | 4-chloro |
| 9 | " | " | 6-chloro |
| 10 | " | C$_2$H$_5$ | 5-CF$_3$ |
| 11 | " | CH$_3$ | 4-CONH$_2$ |
| 12 | 2-aminopyridin-6-yl | CH$_3$ | 4-CONH$_2$ |
| 13 | " | —C(CH$_3$)$_2$COOH | 4-CONH$_2$ |
| 14 | 2-aminopyrimidin-5-yl | CH$_3$ | 4-formyl |
| 15 | 2-aminopyrimidin-5-yl | —C(CH$_3$)$_2$COOH | 4-acetyl |
| 16 | 2-aminopyrazol-5-yl | CH$_3$ | 4-hydroxymethyl |
| 17 | " | —C(CH$_3$)$_2$CH$_2$COOH | 5-carboxy |
| 18 | " | —C(O)NHCH$_3$ | 4-CONH$_2$ |
| 19 | 2-aminothiazol-4-yl | CH$_3$ | 4-N(CH$_3$)$_2$ |
| 20 | " | —C(O)NHCH$_3$ | 6-cyano |
| 21 | 5-amino-1,2,4-thiadiazol-3-yl | CH$_3$ | 4-CONH$_2$ |

-continued

| Example No. | R' | R'' | R$_2$ |
|---|---|---|---|
| 22 | 5-amino-1,2,4-thiadiazol-3-yl | —CH$_2$COOH | 5-SO$_2$NH$_2$ |
| 23 | 5-amino-1,2,4-thiadiazol-3-yl | —CH(C$_2$H$_5$)COOH | 7-OH |
| 24 | 4-aminopyrimidin-2-yl | CH$_3$ | 3-ethyl |
| 25 | 4-aminopyrimidin-2-yl | —C(O)NHC$_2$H$_5$ | 8-OCH$_3$ |
| 26 | 2-aminothiazol-4-yl | CH$_3$ | 4-ethoxy |
| 27 | " | —CH(CH$_3$)$_2$ | 5-bromo- |
| 28 | pyrazol-5-yl | H | H |
| 29 | " | CH$_3$ | H |
| 30 | " | CH$_2$COOC$_2$H$_5$ | H |
| 31 | " | CH$_2$COOC$_2$H$_5$ | 8-OH |

I claim:
1. A compound of the formula

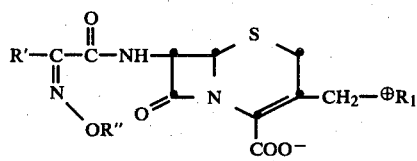

wherein R' is an amino-substituted heterocyclic ring represented by the formulas

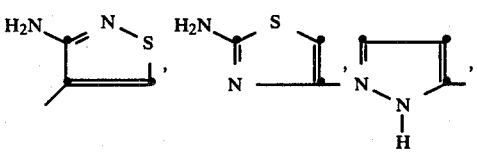

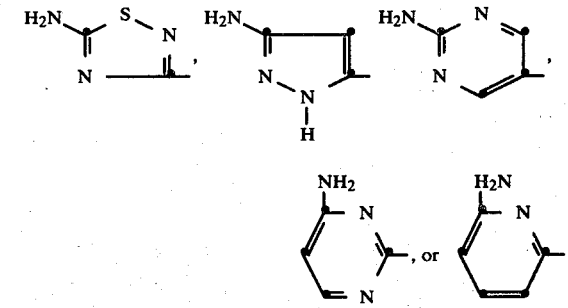

R'' is C$_1$–C$_4$ alkyl, a carboxy-substituted alkyl or a carboxy-substituted cycloalkyl group represented by the formula $$-\overset{a}{\underset{b}{C}}-(CH_2)_n-COR'''$$

wherein a and b independently are hydrogen or $C_1$-$C_3$ alkyl, and a and b when taken together with the carbon atom to which they are bonded form a $C_3$-$C_7$ carbocyclic ring; n is 0–3; and R''' is hydroxy, amino or $C_1$-$C_4$ alkoxy;

$R_1$ is isoquinolinium substituted by amino, $C_1$-$C_4$ alkylamino, di-($C_1$-$C_4$)alkylamino, hydroxy, sulfo, or aminosulfonyl; and the pharmaceutically acceptable non-toxic salts thereof.

2. The compound of claim 1 wherein R'' is $C_1$-$C_4$ alkyl.

3. The compound of claim 1 wherein R'' is a group of the formula $$-\overset{a}{\underset{b}{c}}-(CH_2)_n-COOR'''$$

4. The compound of claim 1 wherein R' is

[chemical structures]

5. The compound of claim 4 wherein R' is

[chemical structures]

6. The compound of claim 5 wherein R'' is $C_1$-$C_4$ alkyl.

7. The compound of claim 4 wherein R'' is a group of the formula $$-\overset{a}{\underset{b}{c}}-(CH_2)_n-COOR'''$$

8. The compound of claim 1 wherein $R_1$ is an amino-substituted isoquinolinium group.

9. The compound of claim 8 wherein R' is

[chemical structures]

10. The compound of claim 9, wherein R' is

[chemical structures]

and R'' is $C_1$-$C_4$ alkyl.

11. The compound of claim 10 said compound being syn-7-[2-(2-aminothiazol-4-yl)-2-methoxyiminoacetaido]-3-(4-aminoisoquinolinium-2-ylmethyl)-3-cephem-4-carboxylate.

12. The compound of claim 10 said compound being syn-7-[2-(2-aminothiazol-4-yl)-2-methoxyiminoacetamido]-3-(5-aminoisoquinolinium-2-ylmethyl)-3-cephem-4-carboxylate.

13. The compound of claim 1 wherein $R_1$ is an hydroxy substituted isoquinolinium group.

14. The compound of claim 13 wherein R' is

[chemical structures]

15. The compound of claim 14 said compound being syn-7-[2-(2-aminothiazol-4-yl)-2-methoxyiminoacetamido]-3-(8-hydroxyisoquinolinium-2-ylmethyl)-3-cephem-4-carboxylate.

16. The compound of claim 14 said compound being syn-7-[2-(2-aminothiazol-4-yl)-2-methoxyiminoacetamido]-3-(5-hydroxyisoquinolinium-2-ylmethyl)-3-cephem-4-carboxylate.

17. The compound of claim 1 wherein $R_1$ is isoquinolinium substituted by a sulfo group.

18. The compound of claim 17 said compound being syn-7-[2-(2-aminothiazol-4-yl)-2-methoxyiminoacetamido]-3-(5-sulfoisoquinolinium-2-ylmethyl)-3-cephem-4-carboxylate.

19. A pharmaceutical formulation comprising a therapeutically effective amount of a compound of claim 1 and a pharmaceutically acceptable diluent.

20. The formulation of claim 19 where in the compound R' is 2-aminothiazol-4-yl or 2-amino-1,3,5-thiadiazol-4-yl and R'' is $C_1$-$C_4$ alkyl.

21. A method for treating bacterial infections in a mammal which comprises administering to said mammal in a dose of between about 100 mg. and about 2000 mg. of a compound of claim 1.

22. The method of claim 21 where in the compound R' is 2-aminothiazol-4-yl or 2-amino-1,3,5-thiadiazol-4-yl, R'' is $C_1$-$C_4$ alkyl, and $R_1$ is an amino-substituted isoquinolinium or an hydroxy-substituted isoquinolinium group.

* * * * *